(12) United States Patent
Rathbun

(10) Patent No.: US 8,940,020 B2
(45) Date of Patent: Jan. 27, 2015

(54) ROD CONNECTOR

(75) Inventor: David S. Rathbun, Gap, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 139 days.

(21) Appl. No.: 13/441,163

(22) Filed: Apr. 6, 2012

(65) Prior Publication Data

US 2013/0268004 A1 Oct. 10, 2013

(51) Int. Cl.
*A61B 17/70* (2006.01)

(52) U.S. Cl.
USPC ............ 606/252; 606/250; 606/251; 606/278

(58) Field of Classification Search
USPC .................................. 606/250–253, 260, 278
See application file for complete search history.

(56) References Cited

U.S. PATENT DOCUMENTS

| | | | |
|---|---|---|---|
| 2,651,766 A | 9/1953 | Runde | |
| 2,712,167 A | 7/1955 | Blanchard | |
| 4,483,334 A | 11/1984 | Murray | |
| 4,707,051 A | 11/1987 | Hall | |
| 5,160,335 A | 11/1992 | Wagenknecht | |
| 5,584,831 A | 12/1996 | McKay | |
| 5,609,593 A | 3/1997 | Errico et al. | |
| 5,624,442 A | 4/1997 | Mellinger et al. | |
| 5,716,355 A | 2/1998 | Jackson et al. | |
| 5,741,252 A | 4/1998 | Mazzio et al. | |
| 5,752,954 A | 5/1998 | Mata et al. | |
| 5,810,814 A | 9/1998 | Newson | |
| 5,810,819 A | 9/1998 | Errico et al. | |
| 5,947,966 A | 9/1999 | Drewry et al. | |
| 5,980,523 A | 11/1999 | Jackson | |
| 5,984,922 A | 11/1999 | McKay | |
| 5,997,539 A | 12/1999 | Errico et al. | |
| 6,015,409 A | 1/2000 | Jackson | |
| 6,022,348 A | 2/2000 | Spitzer | |
| 6,022,350 A | 2/2000 | Ganem | |
| 6,080,153 A | 6/2000 | Mata et al. | |
| 6,096,039 A | 8/2000 | Stoltenberg et al. | |
| 6,217,578 B1 | 4/2001 | Crozet et al. | |
| 6,238,396 B1 | 5/2001 | Lombardo | |
| 6,261,288 B1 | 7/2001 | Jackson | |

(Continued)

FOREIGN PATENT DOCUMENTS

| | | |
|---|---|---|
| EP | 143789 A1 | 6/1985 |
| EP | 1397999 A1 | 3/2004 |

(Continued)

OTHER PUBLICATIONS

Synthes, Inc., Product Guide, "MATRIX Spine System. Snap-On Transconnectors.", (Nov. 2010), 8 pages.

(Continued)

*Primary Examiner* — Mary Hoffman
*Assistant Examiner* — Christina Negrellirodrigue
(74) *Attorney, Agent, or Firm* — Meunier Carlin & Curfman, LLC

(57) ABSTRACT

A connector for engaging two or more rods is disclosed. The connector includes a main body, at least two medial bodies and a compression mechanism. Generally, the connector provides for easy "snap-fit" lateral insertion of the rods into rod openings defined between the medial bodies and the main body. The snap-fit is achieved through a spring bias exerted by the compression mechanism. The compression mechanism may also be configured to lock the rods within the openings, such as through the use of a fastener.

23 Claims, 5 Drawing Sheets

(56) References Cited

U.S. PATENT DOCUMENTS

| | | |
|---|---|---|
| 6,342,054 B1 | 1/2002 | Mata |
| 6,371,957 B1 | 4/2002 | Amrein et al. |
| 6,468,276 B1 | 10/2002 | McKay |
| 6,554,831 B1 | 4/2003 | Rivard et al. |
| 6,616,668 B2 | 9/2003 | Altarac et al. |
| 6,761,721 B2 | 7/2004 | Burgess et al. |
| 6,872,208 B1 | 3/2005 | McBride et al. |
| 6,887,241 B1 | 5/2005 | McBride et al. |
| 7,066,938 B2 | 6/2006 | Slivka et al. |
| 7,166,109 B2 | 1/2007 | Biedermann et al. |
| 7,207,992 B2 | 4/2007 | Ritland |
| 7,481,827 B2 | 1/2009 | Ryan et al. |
| 7,491,008 B2 | 2/2009 | Thomke et al. |
| 7,569,070 B2 | 8/2009 | Suzuki et al. |
| 7,572,278 B2 | 8/2009 | Suzuki et al. |
| 7,666,210 B2 | 2/2010 | Franck et al. |
| 7,695,498 B2 | 4/2010 | Ritland |
| 7,744,633 B2 | 6/2010 | Berrevoets et al. |
| 7,806,623 B2 | 10/2010 | Thomke et al. |
| 7,806,912 B2 * | 10/2010 | Lawton et al. ............... 606/250 |
| 7,985,245 B2 | 7/2011 | Ritland |
| 8,226,689 B2 | 7/2012 | Jones et al. |
| 8,246,657 B1 * | 8/2012 | Samuel ...................... 606/250 |
| 8,454,661 B2 | 6/2013 | Rathbun et al. |
| 2003/0114853 A1 | 6/2003 | Burgess et al. |
| 2003/0153917 A1 * | 8/2003 | Richelsoph et al. ........... 606/61 |
| 2004/0133202 A1 | 7/2004 | Suzuki et al. |
| 2004/0138659 A1 | 7/2004 | Austin et al. |
| 2005/0090821 A1 | 4/2005 | Berrevoets et al. |
| 2005/0113831 A1 | 5/2005 | Franck et al. |
| 2005/0228377 A1 | 10/2005 | Chao et al. |
| 2006/0079899 A1 | 4/2006 | Ritland |
| 2006/0149231 A1 | 7/2006 | Bray |
| 2006/0247629 A1 | 11/2006 | Maughan et al. |
| 2007/0118124 A1 | 5/2007 | Biedermann et al. |
| 2007/0135817 A1 | 6/2007 | Ensign |
| 2007/0161987 A1 | 7/2007 | Capote et al. |
| 2007/0219556 A1 * | 9/2007 | Altarac et al. ............... 606/64 |
| 2007/0233066 A1 | 10/2007 | Rezach |
| 2008/0312696 A1 | 12/2008 | Butters et al. |
| 2009/0099604 A1 | 4/2009 | Cho et al. |
| 2009/0148232 A1 | 6/2009 | Thomke et al. |
| 2009/0287253 A1 | 11/2009 | Felix et al. |
| 2010/0168796 A1 | 7/2010 | Eliasen et al. |
| 2010/0204733 A1 | 8/2010 | Rathbun et al. |
| 2010/0211100 A1 | 8/2010 | Mack |
| 2010/0268279 A1 | 10/2010 | Gabelberger et al. |
| 2013/0072991 A1 | 3/2013 | Rathbun et al. |
| 2013/0253586 A1 | 9/2013 | Rathbun et al. |

FOREIGN PATENT DOCUMENTS

| | | |
|---|---|---|
| EP | 1690505 A1 | 8/2006 |
| ES | 2313208 T3 | 8/2006 |
| KR | 20040024493 A | 3/2004 |
| WO | 03034930 A1 | 5/2003 |
| WO | 2005044117 A2 | 5/2005 |
| WO | 2009042653 A1 | 4/2009 |

OTHER PUBLICATIONS espace.net, Abstract of FR2856578, published Dec. 31, 2004, by Luc et al.

espace.net, Abstract of JP2007526007, published Sep. 13, 2007, by DePuy Spine Inc.

espace.net, Abstract of KR100617378, published Mar. 20, 2004, by Nobumasa et al.

* cited by examiner

ROD CONNECTOR

BACKGROUND

Surgeons often use rods, screws and other devices to support or fix various hard tissues, such as for the fusion of spinal vertebrae during orthopedic surgery. Orthopedic surgeons will also often need to connect or combine two or more adjacent rods to reduce mobility of the spine or other bones. They can use connector blocks to attach rods. Conventional connector blocks, often called "dominoes," are normally closed through holes in a block held tight with up to four set screws.

Current uses of dominoes include revision surgeries to lengthen existing fixation constructs. Surgeons may also use dominoes to reinforce high stress areas in posterior constructs. Dominoes may also be used for branching to supplement fixation points or as a narrow trans-connector.

Despite the usefulness of dominoes, they are still amendable to some improvements. For example, they can be clumsy or difficult to deploy. Slight bends in the rods can preclude the use of domino connector blocks because of the tight tolerance of the through holes.

SUMMARY

Implementations of the present disclosure overcome the problems of the prior art by providing a connector for engaging a pair of rods. The connector includes a main body, at least two upper bodies to be further known as medial bodies and a compression mechanism. The main body includes a pair of opposite sides. Each of the opposite sides defines a first rod gripping surface. The first rod gripping surface is configured to extend at least partially over an outside surface of one of the rods. Each of the medial bodies has a free end and defines a second rod gripping surface. The second rod gripping surface is configured to extend at least partially over an outside surface of one of the rods.

The compression mechanism is configured to hold each of the medial bodies against a respective one of the opposite sides of the main body. They are held such that each pair of the first and second rod gripping surfaces defines a rod opening. The rod opening has an opening axis. And, the free end of the medial body is spaced away from the main body a distance less than or equal to a diameter of the one of the rods. The compression mechanism may be further configured to simultaneously urge the free end of each of the medial bodies toward the main body so as to shrink the distance.

The compression mechanism may include one or more ramp surfaces. The ramp surfaces, for example, may extend between each of the medial bodies and an adjacent one of the opposite sides of the main body. The ramp surfaces may extend at an angle relative to a plane containing or falling between the opening axis of each of the pair of first and second rod gripping surfaces.

The compression mechanism may also include a shaft extending through an opening in each of the medial bodies and the main body. Also, the compression mechanism may further include a spring bias, such as by use of one or more spring washers extending around the shaft. The compression mechanism may also include a fastener with a head and the shaft. For the fastener, the spring washer is positioned between the head and one of the medial bodies.

The compression mechanism may also include a nut configured to attach to an end of the shaft opposite the head. This holds the main and medial bodies between the nut and the head. The nut may include threads configured to mate with threads on the shaft.

The compression mechanism may also include a plurality of spring washers, fasteners and nuts.

The rod opening can have different shapes, such as a cylindrical shape or a square or rectangular shape to fit different rod shapes.

Also, a connector may include a compression mechanism that is configured to simultaneously urge the medial bodies along vectors extending at an angle to a plane. The plane contains the opening axis of each pair of first and second rod gripping surfaces.

The vectors, for example, may be equal in orientation and opposite in magnitude. They may also have offset origins.

A method of engaging a pair of rods includes holding a pair of medial bodies against opposite sides of a main body. This forms a pair of rod openings on opposite sides of the main body. Also, the medial bodies are urged against opposite sides of the main body. The method also includes receiving pressure from a lateral portion of a first one of the rods. The pressure is received between a free end of a first one of the medial bodies and the main body. And, the method includes responding to the pressure by sliding the first medial body along a first ramp surface. The first ramp surface is oriented at an angle to a plane passing through axes of the rod openings. Sliding lateral to medial widens the distance between the free end of the first medial body and the main body.

The method may also include receiving the first rod into a first one of the rod openings. After receiving the first rod, the first rod is trapped by urging the first medial body medial to lateral back along the first ramp surface. This shrinks the distance between the free end of the first medial body and the main body.

The method may also include receiving pressure from a lateral portion of a second one of the rods between a free end of a second one of the medial bodies and the main body. The pressure is responded to by sliding the second medial body along a second ramp surface. This widens a distance between the free end of the second medial body and the main body.

Also, the second rod may be received into a second one of the rod openings. And, the second medial body may be urged back along the second ramp surface. This traps the second rod within the second opening.

The method may also include receiving compression on outer surfaces of the first and second medial bodies. The outer surfaces are opposite one another and the compression locks the first and second rods within their respective openings.

These and other features and advantages of the implementations of the present disclosure will become more readily apparent to those skilled in the art upon consideration of the following detailed description and accompanying drawings, which describe both the preferred and alternative implementations of the present disclosure.

DETAILED DESCRIPTION

Figure 1:
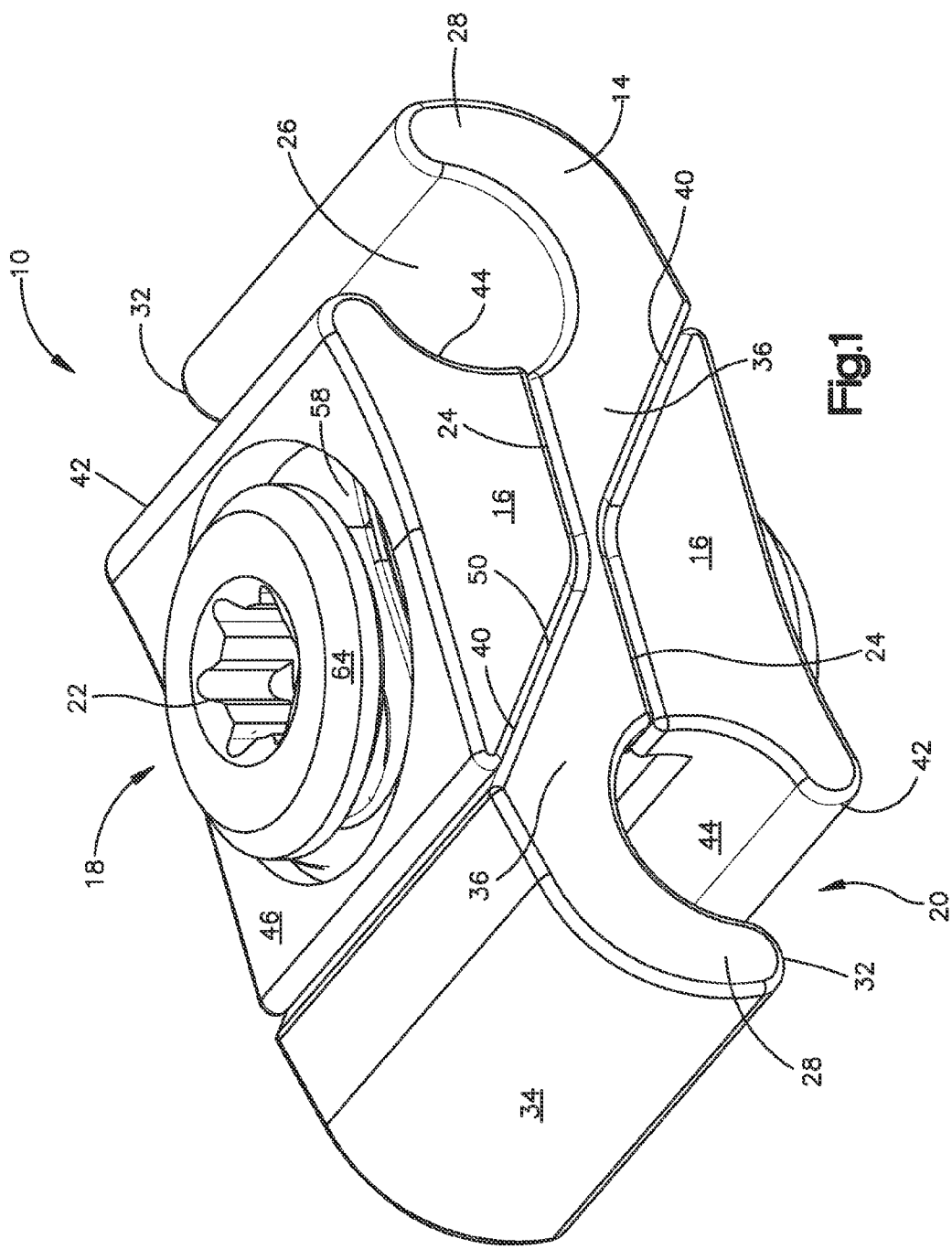
FIG. 1 is a perspective view of a connector for connecting two rods.

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

A connector 10 for engaging two or more rods 12 is shown in FIGS. 1-5. The connector 10 includes a main body 14, at least two medial bodies 16 and a compression mechanism 18. Generally, the connector 10 provides for easy "snap-fit" lateral insertion of the rods 12 into rod openings 20 defined between the medial bodies 16 and the main body 14. The snap-fit is achieved through a spring bias exerted by the compression mechanism 18. The compression mechanism 18 may also be configured to lock the rods 12 within the openings, such as through the use of a fastener 22.

Although described herein as being used in orthopedic surgery, the connector 10 could be used in other surgical or non-surgical settings. For example, two adjacent cylindrical pipelines could be combined using the connector 10.

Figure 4:
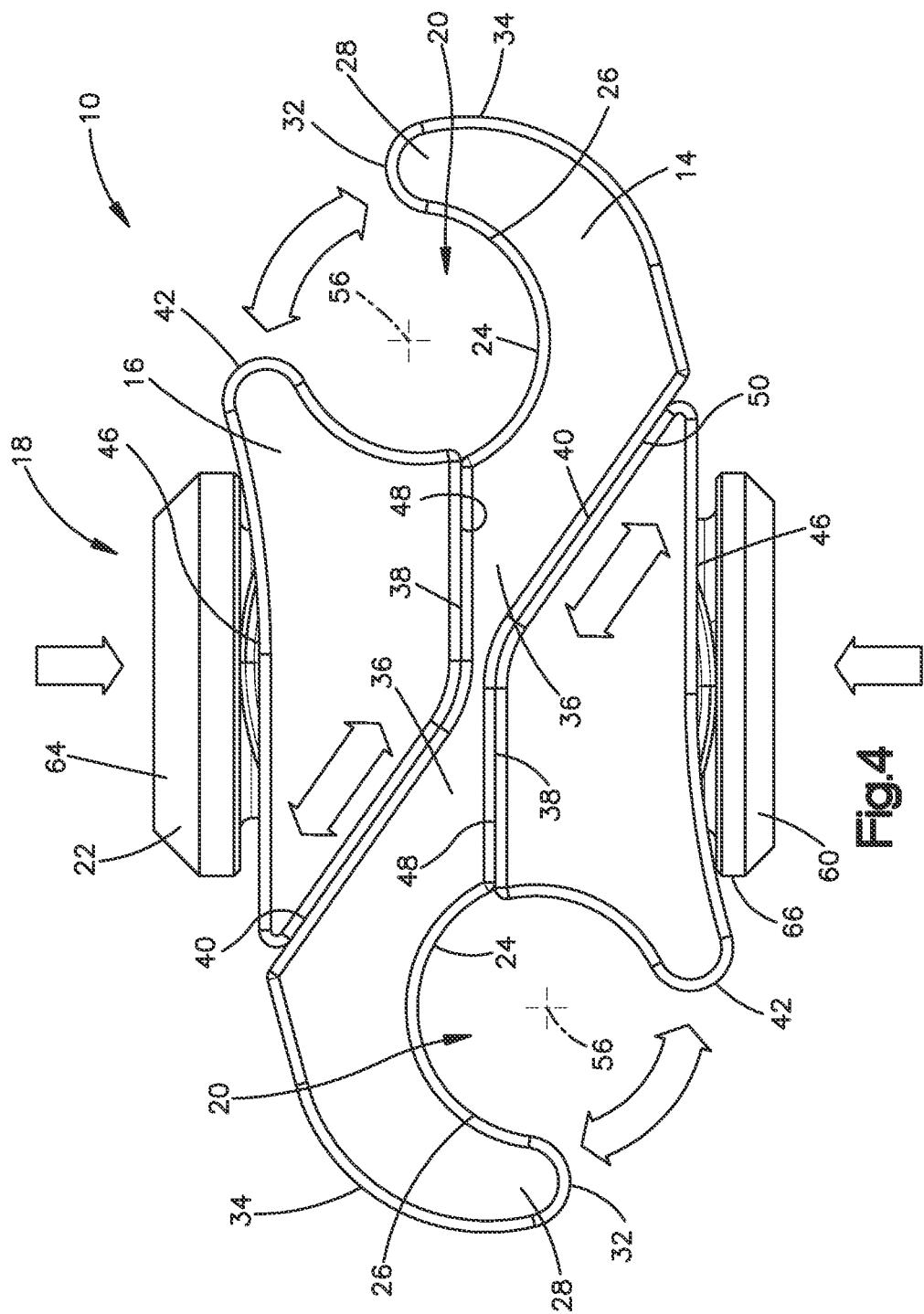
FIG. 4 is a schematic showing movement vectors of components of the connector of FIG. 1.
Figure 5:
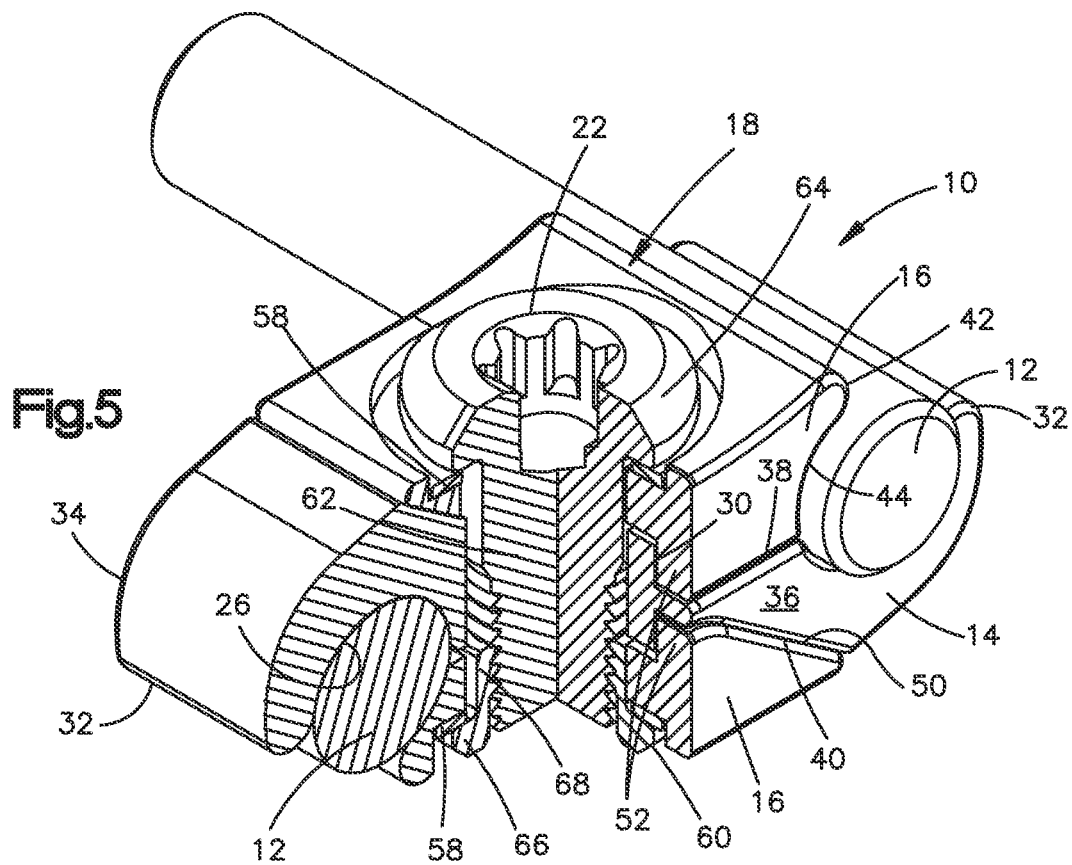
FIG. 5 is a sectional view of the connector of FIG. 1 with two rods connected.

As shown in FIG. 1, the main body 14 includes a pair of opposite sides 24. Each of the opposite sides 24 defines a first rod gripping surface 26. The first rod gripping surface 26 is configured to extend at least partially over an outside surface of one of the rods 12, as shown in FIG. 5. The first rod gripping surface 26, for example, has a concave arc shape that is configured to conform to a portion of an outer surface of the cylindrical shaped rod 12 shown herein. As shown in FIG. 4, the arc portion is, in cross-section, more than 90 degrees but less than 180 degrees. For example, as shown in FIG. 4, the arc portion is about 60 to 80 degrees.

Although illustrated as a concave arc portion, the first rod gripping surface 26 may be a range of shapes and sizes in order to adapt to different expected rod shapes. For example, the first rod gripping surface 26 may have a right angle to grip a square or rectangular rod. Or, it may have an elliptical arc portion to grip oval shaped rods.

The first rod gripping surfaces 26 are supported by hook members 28 of the main body 14 that extend laterally opposite from a center plane of the connector 10. The first rod gripping surfaces 26 are positioned on the opposite sides 24, causing the hook members 28 to face in opposite directions. Thus, the main body 14 is asymmetrical about the center plane.

Figure 3:
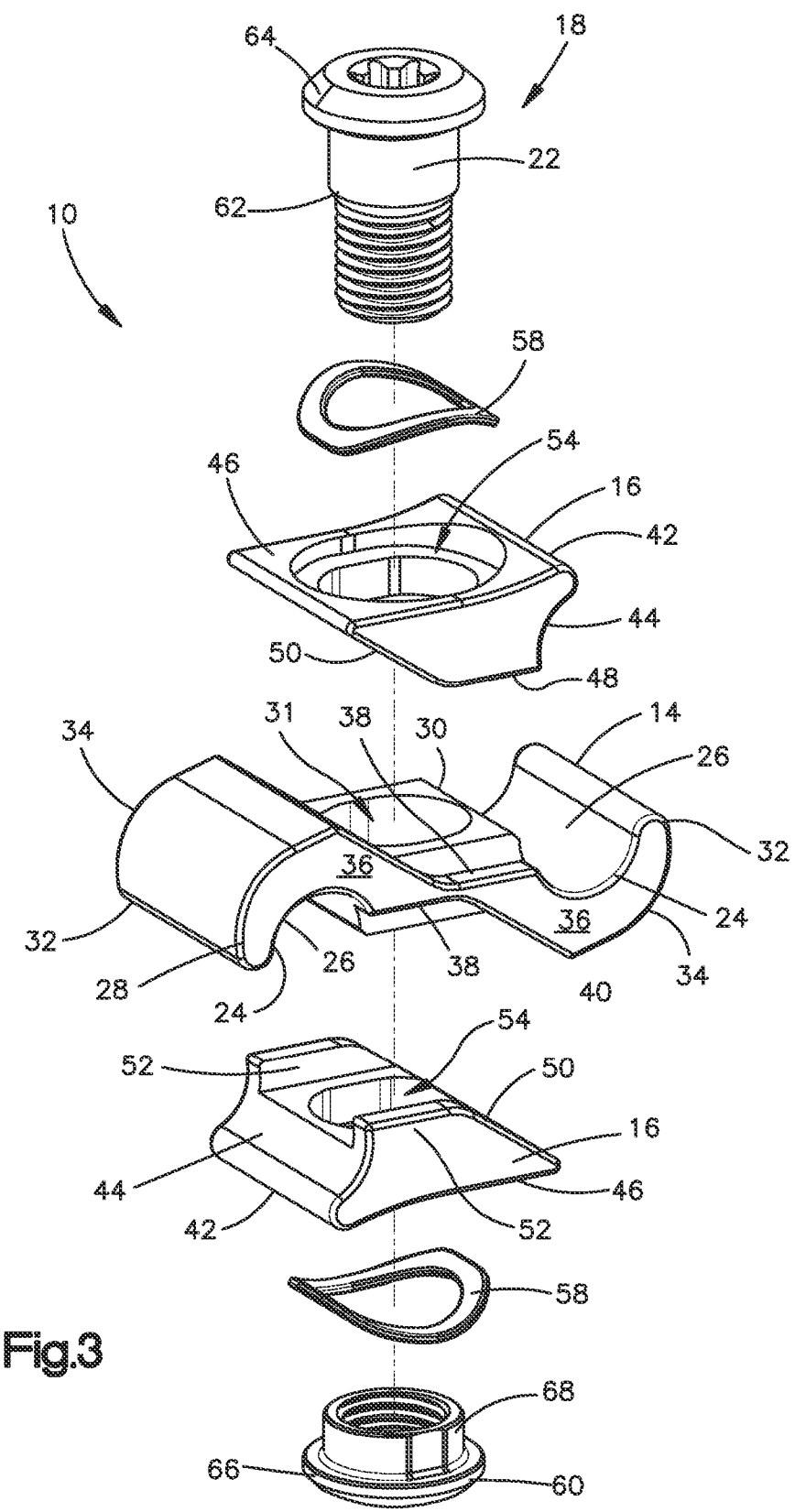
FIG. 3 is an exploded view of the connector of FIG. 1.

As shown by FIG. 3, the main body also includes a center block 30 that has a rectangular block shape from which the hook members 28 extend laterally. The block shape is formed by pairs of parallel flat surfaces, such as top and bottom surfaces. Defined in the center block 30 is a cylindrical or oval opening 31. The cylindrical opening 31 extends between the top and bottom surfaces. The hook members 28 extend from and around the lateral parallel surfaces that form the center block 30.

As shown in FIG. 4, the hook members 28 include rounded free ends 32 that have a smooth cam-like structure for lateral acceptance of the rods 12 as will be described more below. Extending around the outside of the hook members 28 are arc-shaped outer hook surfaces that have a slightly more gradual curvature than the first rod gripping surfaces 26.

Each of the hook members 28 also includes a wedge portion 36 that extends from the inner and outer curved surfaces and surrounds and connects to the center block 30. The wedge portion includes both a flat surface 38 and a ramp surface 40. The flat surface 38 extends orthogonal to the axis of the center block opening 31. The ramp surface 40 is angled with respect to the flat surface 38. The ramp surface 40 extends between the first rod gripping surface 26 of its own hook member 28 and the flat surface 38 of the other hook member 28. As described below, the flat and ramp surfaces 38, 40 may be part of the compression mechanism 18 and keeps the medial bodies orientated to main body.

Each of the medial bodies 16 has a free end 42 and defines a second rod gripping surface 44. As shown in FIG. 5, the second rod gripping surface 44 is configured to extend at least partially over an outside surface of one of the rods 12. For example, in the case of the cylindrical rods 12, the second rod gripping surface 44 has a concave, arc shape that is about a 20 degree to 45 degree, or about 30 degree, arc portion of a cylindrical rod outer surface.

The free end 42 is on the end of a short hook member of the medial body 16. The free end 42 of the short hook member extends slightly upward from a flat outer surface 46 of the medial body. The free ends 42 have a rounded cam-like structure similar to the free ends 32 of the main body 14.

Each of the medial bodies also includes the outer surface 46 and inner surfaces 48. The outer and inner surfaces 46, 48 are flat and parallel to each other, as shown in FIG. 3. Each medial body 16 also includes a ramp surface 50 configured to mate with and slide along the ramp surface 40 of the main body 14, as will be described below. The ramp surface 50 has a similar angle range as that of the ramp surface 40.

Each medial body 16 also includes a pair of legs or flanges 50 extending interiorly to form a channel or orientation recess within which the center block 30 is configured to slide. The flanges 50 are configured to inhibit lateral sliding of the medial bodies 16 relative to the center block 30. The top edges of the flanges 50 include portions of the flat inner surfaces 48. Also, the base of the channel includes the flat inner surfaces 48.

Defined by each medial body 16 is an opening 54 extending between the outer surface 46 and the inner surface 48 of the channel between the flanges 50, as shown in FIGS. 3 and 5. The openings 54 have a slightly elongated slot shape that facilitates their sliding mobility as will be described below. When assembled, the openings 31, 54 of the main body 14 and medial bodies 16 are sufficiently aligned to allow passage of a fastener.

Additionally, each medial body may define a circular recess in its outer surface 46 for receipt of a spring washer 58.

The compression mechanism 18 is configured to hold each of the medial bodies 16 against a respective one of the opposite sides 24 of the main body 14. They are held such that each pair of the first and second rod gripping surfaces 26, 44 defines a rod opening. The rod opening has an opening axis 56, as shown in FIG. 4. When assembled, for example, the free end 42 is spaced away from the free end 32 of the adjacent hook member 18 a distance less than or equal to a diameter of one of the rods 12.

As shown in FIG. 5, the compression mechanism 18 may include selected aspects of the main body 14 and the medial bodies 16. The compression mechanism 18, for example, may include the ramp surfaces 40, 50 and flat surfaces 38, 48 that contribute to the relative motion of the medial bodies with respect to the main body. Also, the compression mechanism 18, as shown in the exploded view of FIG. 3, may include a fastener or clamping screw 22, a pair of the spring washers 58 and a nut 60.

The clamping screw 22 includes a shaft 62 and a head 64. The head 64 includes a drive feature. The shaft 62 includes a non-threaded portion and a smaller diameter threaded portion. The nut 60 has a flange 66 with smaller diameter protrusion 68 extending from the flange. The protrusion 68 has parallel flats for de-rotation and internal threads with a counter bore from its flanged side, as shown in FIG. 5. The spring washers 58 are arched rings made of high stress-strain material that are formed in a "potato chip" shape. Bias could also be applied by other types of springs, such as coil or cantilever springs.

The compression mechanism 18 may be configured to simultaneously urge the free end 42 of the medial bodies 16 toward the main body 14 so as to shrink the distance between the free ends 32 and 42. As shown in FIG. 5, when assembled, the shaft 62 of the clamping screw 22 extends through both slot openings 54 and the center block opening 31 in the main body 14. The nut 60 is threaded on the end of the shaft 62 of the clamping screw 22, opposite a head 64 of the clamping screw with the bodies 14 and 16 positioned between them. One of the spring washers 58 is positioned between the head 64 and the immediately adjacent medial body 16. The other of the spring washers 58 is positioned between the nut 60 and the immediately adjacent medial body 16.

In an assembled, preset condition the two spring washers 58 apply an axial load compressing the upper (and lower) medial bodies 16 towards the main body 14. The angled or ramp surfaces 40, 50 direct the upper medial body down and to the right (medial to lateral), as shown in FIG. 4. The lower medial body 16 moves up and to the left, in a direction opposite the upper medial body. The flanges 52 on each of the medial bodies 16 extend along the flat sides of the center block 30 to maintain the outer and main body orientations.

During deployment, the introduction of a spine rod 12 causes the opening between the medial body 16 and main body 14 to spread apart. The upper body 16 moves with increased resistance, against the bias of the spring washers 58, up and away (lateral to medial) from the rod slot 20. Once the widest part of the rod 12's diameter passes the narrowest part of the rod opening 20, the rod will be drawn into the channel under the bias of the spring washers 58 causing the snap effect.

The compression load generated by the spring washers 58 prevents the rod 12 from falling out of the channel 20. An external force must overcome the force generated by spring washers 58 to remove the rod 12 from the channel 20.

Figure 6:
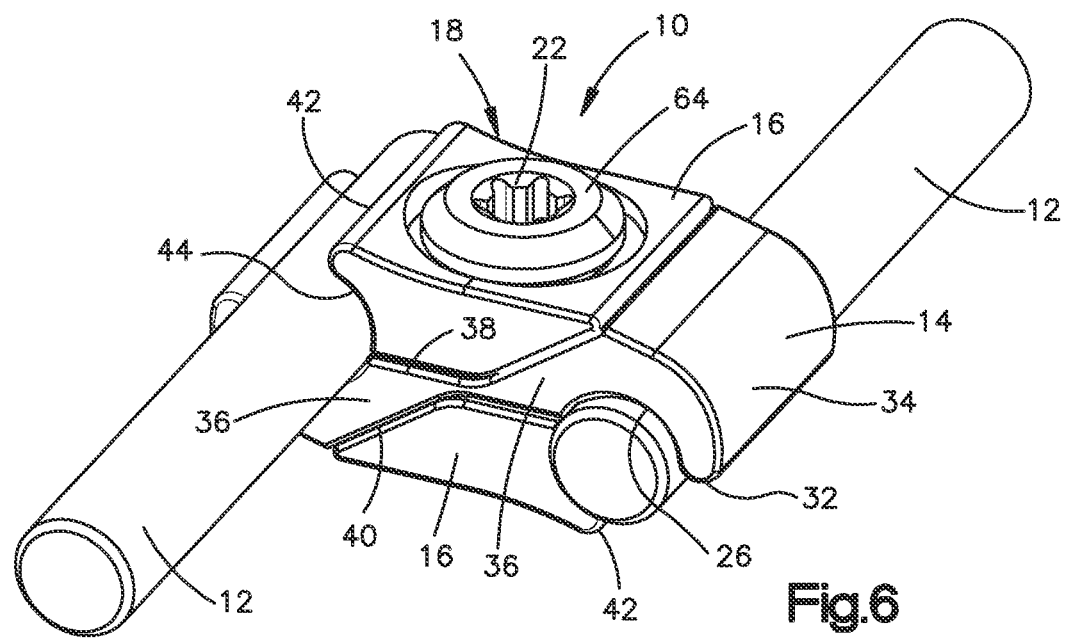
FIG. 6 is a perspective view of the connector of FIG. 1 with two rods connected.

As shown in FIG. 6, both rods 12 are introduced and the implant device positioned as needed. The clamping screw or fastener 22 is tightened to a predetermined torque drawing the lower nut 60 up which compresses the spring washers 58, as shown in FIG. 4. The compression forces the upper (and lower) medial bodies 16 towards the horizontal midline or plane and away from the vertical midline or plane of the main body 14. This compresses the rods 12 in the channels 20 and prevents movement.

FIG. 4 includes arrows showing the motion of the clamping screw 22 and nut 60 in compression. Vectors extending at an angle to the midline plane show the motion of the medial bodies 16. The vectors defining the motion of medial bodies 16, for example, are equal in orientation and opposite in magnitude. They may also have offset origins.

In FIG. 4, additional vectors along an arc illustrate the motion of the free ends 32, 42 of the medial bodies 16 and main body hook members 28.

Figure 2:
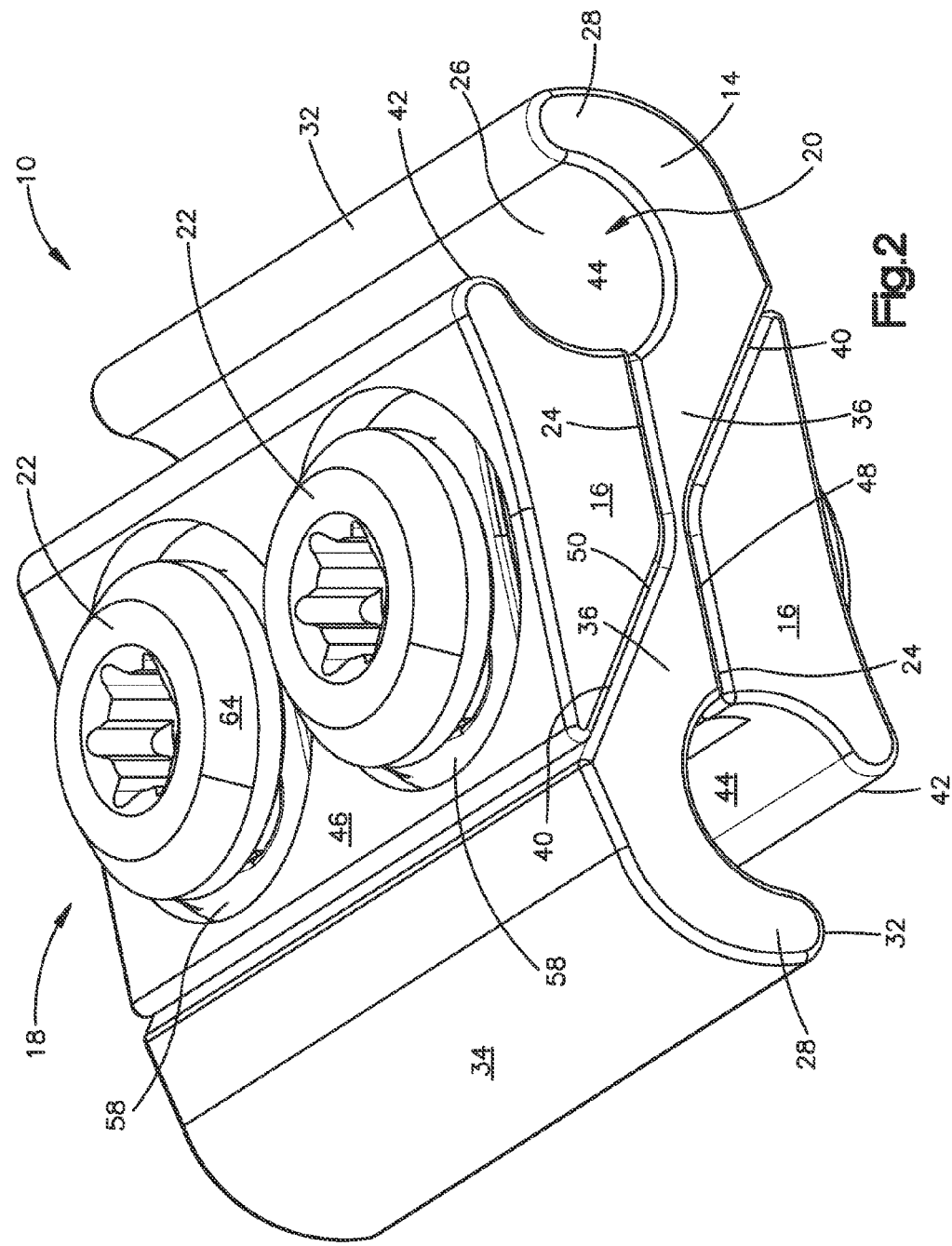
FIG. 2 is a perspective view of a double-length connector for connecting two rods.

FIG. 2 shows a connector 10 that includes two sets of fasteners 22 and associated spring washers 58 and an additional nut 60. This facilitates use of longer bodies 14 and 16 for longer rod openings 20. The length of the connector 10 and number of rods it will accept can be varied as desired. Thus, the number and configuration of compression mechanism 18 components may be varied. Other variations of the connector 10 include variations and size, number and type of rods 12 being connected. For example, square or elliptical cross-section rods may be connected. Also, rods of different sizes may be connected. The Advantages include the open lateral sides of the slots 20 facilitate easier attachment on revision surgeries. Further, the connector 10 has some adaptability (without changing components) to bent rods or different size rods that are not easily secured by prior art dominoes. The number of fasteners, one or two, are reduced over similarly scaled conventional dominoes. Also, clamping forces are distributed over larger areas with fewer stress risers.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A connector for engaging a pair of rods, the connector comprising:
   a main body including opposite upper and lower sides, the upper and lower sides extending in a direction transverse to a vertical axis of the connector, each of the opposite upper and lower sides defining a first rod gripping surface configured to extend at least partially over an outside surface of one of the rods;
   at least two medial bodies, each of the medial bodies having a free end and defining a second rod gripping surface configured to extend at least partially over an outside surface of one of the rods; and
   a compression mechanism configured to hold each of the medial bodies against a respective one of the opposite upper and lower sides of the main body so that each pair of first and second rod gripping surfaces defines a rod opening having an opening axis and wherein the free end is spaced away from the main body a distance less than or equal to a diameter of the one of the rods;
   wherein the rod openings include an upper rod opening and a lower rod opening oriented on opposite sides of a plane defined transverse to the vertical axis of the connector,
   wherein the compression mechanism is further configured to simultaneously urge the free end of each of the medial bodies toward the main body so as to shrink the distance.

2. A connector of claim 1, wherein the compression mechanism includes a ramp surface extending from each of the medial bodies and a corresponding ramp surface extending from the opposite sides of the main body.

3. A connector of claim 2, wherein the ramp surfaces extend at an angle relative to a plane falling between the opening axis of each pair of first and second rod gripping surfaces.

4. A connector of claim 3, wherein the compression mechanism includes a shaft extending through an opening in each of the medial bodies and the main body.

5. A connector of claim 4, wherein the compression mechanism further includes a spring bias.

6. A connector of claim 5, wherein the spring bias includes a spring washer extending around the shaft.

7. A connector of claim 6, wherein the compression mechanism includes a fastener and the fastener includes a head and the shaft.

8. A connector of claim 7, wherein the spring washer is positioned between the head and one of the medial bodies.

9. A connector of claim 8, wherein the compression mechanism includes a nut configured to attach to an end of the shaft opposite the head and to hold the main and medial bodies between the nut and head.

10. A connector of claim 9, wherein the nut has threads configured to mate with threads on the shaft.

11. A connector of claim 10, wherein the compression mechanism includes at least two spring washers, fasteners and nuts.

12. A connector of claim 1, wherein the rod opening has a cylindrical shape and extends in a direction along the vertical axis of the connector.

13. A connector for engaging a pair of rods, the connector comprising:
    a main body including opposite upper and lower sides, the upper and lower sides extending in a direction transverse to a vertical axis of the connector, each of the opposite upper and lower sides defining a first rod gripping surface configured to extend at least partially over an outside surface of one of the rods;
    at least two medial bodies, each of the medial bodies having a free end and defining a second rod gripping surface configured to extend at least partially over an outside surface of one of the rods; and
    a compression mechanism configured to hold each of the medial bodies against a respective one of the opposite upper and lower sides of the main body so that each pair of first and second rod gripping surfaces defines a rod opening having an opening axis and wherein the free end is spaced away from the main body a distance less than or equal to a diameter of the one of the rods;
    wherein the rod openings include an upper rod opening and a lower rod opening oriented on opposite sides of a plane defined transverse to the vertical axis of the connector,
    wherein the compression mechanism is further configured to simultaneously urge the medial bodies along vectors extending at an angle to a plane falling between or containing the opening axis of each pair of first and second rod gripping surfaces.

14. A connector of claim 13, wherein the vectors are opposite in magnitude.

15. A connector of claim 14, wherein the vectors are equal in orientation.

16. A connector of claim 15, wherein the vectors have offset origins.

17. A method of engaging a pair of rods, the method comprising:
    holding a pair of medial bodies against opposite upper and lower sides of a main body to form a pair of rod openings on opposite upper and lower sides of the main body, where the upper and lower sides of the main body extend in a direction transverse to a vertical axis of the main body, where the pair of rod openings including an upper rod opening and a lower rod opening oriented on opposite sides of a plane defined transverse to the vertical axis of the main body;
    urging the medial bodies against the opposite upper and lower sides of the main body;
    receiving pressure from a lateral portion of a first one of the rods between a free end of a first one of the medial bodies and the main body; and
    responding to the pressure by sliding the first medial body along a first ramp surface oriented at an angle to a plane passing through axes of the rod openings and widening a distance between the free end of the first medial body and the main body.

18. A method of claim 17, further comprising receiving the first rod into a first one of the rod openings.

19. A method of claim 18, further comprising urging the first medial body back along the first ramp surface to shrink the distance between the free end of the first medial body and the main body and trap the first rod within the first opening.

20. A method of claim 19, further comprising receiving pressure from a lateral portion of a second one of the rods between a free end of a second one of the medial bodies and the main body and responding to the pressure by sliding the second medial body along a second ramp surface and widening a distance between the free end of the second medial body and the main body.

21. A method of claim 20, further comprising receiving the second rod into a second one of the rod openings.

22. A method of claim 21, further comprising urging the second medial body back along the second ramp surface to trap the second rod within the second opening.

23. A method of claim 22, further comprising receiving compression on outer surfaces of the first and second medial bodies, wherein the outer surfaces are opposite one another, and locking the first and second rods within their respective openings.

* * * * *